United States Patent [19]

Engel et al.

[11] Patent Number: 5,710,145
[45] Date of Patent: Jan. 20, 1998

[54] PROTEIN KINASE C INHIBITOR

[75] Inventors: Gary Lowell Engel, Greenwood; Nagy Alphonse Farid, Lebanon; Margaret Mary Faul, Zionsville; Michael Robert Jirousek; Lori Ann Richardson, both of Indianapolis; Leonard Larry Winneroski, Jr., Greenwood, all of Ind.

[73] Assignee: Eli Lilly and Company, Indianapolis, Ind.

[21] Appl. No.: 749,607

[22] Filed: Nov. 18, 1996

Related U.S. Application Data

[60] Provisional application No. 60/006,970, Nov. 20, 1995.

[51] Int. Cl.$^6$ ............ A61K 31/395; C07D 419/00
[52] U.S. Cl. ............ 514/183; 540/469; 514/185
[58] Field of Search ............ 514/183; 540/469

[56] References Cited

U.S. PATENT DOCUMENTS

| | | | |
|---|---|---|---|
| 5,057,614 | 10/1991 | Davis et al. | 548/466 |
| 5,292,747 | 3/1994 | Davis et al. | 514/285 |
| 5,552,396 | 9/1996 | Heath, Jr. et al. | 514/183 |

FOREIGN PATENT DOCUMENTS

| | | | |
|---|---|---|---|
| 0 657 458 A | 6/1995 | European Pat. Off. | |
| WO 94/07895 | 4/1994 | WIPO | C07D 487/22 |

OTHER PUBLICATIONS

DeFronzo, R.A., "Diabetic Nephropathy: Etiologic and Therapeutic Considerations", *Diabetes Reviews*, vol. 3, No. 3, 510–564, 1995.

Inoguchi, et al., "Preferential Elevation of Protein Kinase C Isoform bII and Diacylglycerol levels in the aorta and heart of diabetic rate: Differential reversibility to glycemic control by islet cell transplantation:", *Proc. Natl. Acad. Sci. USA*, vol. 89, 11059–11063, Nov. 1992.

Ishii, et al., "Amelioration of Vascular Dysfunctions in Diabetic Rats by an Oral PKC b Inhibitor:", *Science*, vol. 272, 728–731, 3 May 1996.

Porte, et al., "Diabetes Complications: Why is Glucose Potentially Toxic?", *Science*, vol. 272, 699–700, 3 May 1996.

Kowluru, et al., "Diabetes-Induced Disorders of Retinal Protein Kinase C and Na, K-ATPase are Inhibited by LY333531", Abstract, American Diabetes Association Meeting Jun. 8–11, 1996.

Ishii, et al., "Treatment with Protein Kinase C b Isoform Inhibitor Normalized Urinary Albumin Excretion and Glomerular Filtration Rate in Diabetic Rats", Abstract, American Diabetes Association Meeting, Jun. 8–11, 1996.

Lee, et al., "Activation of protein kinase C by elevation of glucose concentration: Proposal for a mechanism in the development of diabetic vascular complications", *Proc. Natl. Acad. Sci. USA*, 86: 5141–5145 1989.

Murray, et al. "Protein Kinases and Phosphates: Structural Biology and Synthetic Inhibitors", Annual Reports in Medicinal Chemistry, San Diego: Academic Press, 1994, vol. 29, Chapter 26, pp. 255–264.

*Primary Examiner*—Mukund J. Shah
*Assistant Examiner*—Pavanaram K. Sripada
*Attorney, Agent, or Firm*—Steven P. Caltrider; David E. Boone

[57] ABSTRACT

This invention provides novel bis-indolylmaleimide macrocycle derivatives of the formula:

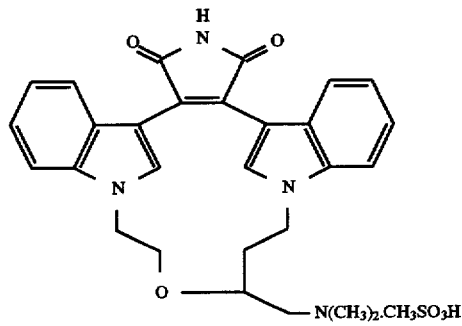

and solvates thereof. The invention further provides the preparation, pharmaceutical formulations and the methods of use for inhibiting Protein Kinase C in mammals.

18 Claims, No Drawings

PROTEIN KINASE C INHIBITOR

This application claims the benefit of U.S. Provisional application Ser. No. 60/006,970, filed Nov. 20, 1995.

BACKGROUND OF THE INVENTION

Protein kinase C (PKC) consists of a family of closely related enzymes that function as serine/threonine kinases. Protein kinase C plays an important role in cell—cell signaling, gene expression, and in the control of cell differentiation and growth. At present, there are currently at least ten known isozymes of PKC that differ in their tissue distribution, enzymatic specificity, and regulation. Nishizuka Y. *Annu. Rev. Biochem.* 58: 31–44 (1989); Nishizuka Y. *Science* 258: 607–614 (1992).

Protein kinase C isozymes are single polypeptide chains ranging from 592 to 737 amino acids in length. The isozymes contain a regulatory domain and a catalytic domain connected by a linker peptide. The regulatory and catalytic domains can be further subdivided into constant and variable regions. The catalytic domain of protein kinase C is very similar to that seen in other protein kinases while the regulatory domain is unique to the PKC isozymes. The PKC isozymes demonstrate between 40–80% homology at the amino acid level among the group. However, the homology of a single isozyme between different species is generally greater than 97%.

Protein kinase C is a membrane-associated enzyme that is allosterically regulated by a number of factors, including membrane phospholipids, calcium, and certain membrane lipids such as diacylglycerols that are liberated in response to the activities of phospholipases. Bell, R. M. and Burns, D. J., *J. Biol. Chem.* 266: 4661–4664 (1991); Nishizuka, Y. *Science* 258: 607–614 (1992). The protein kinase C isozymes, alpha, beta-1, beta-2 and gamma, require membrane phospholipid, calcium and diacylglycerol/phorbol esters for full activation. The delta, epsilon, eta, and theta forms of PKC are calcium-independent in their mode of activation. The zeta and lambda forms of PKC are independent of both calcium and diacylglycerol and are believed to require only membrane phospholipid for their activation.

Only one or two of the protein kinase C isozymes may be involved in a given disease state. For example, the elevated blood glucose levels found in diabetes lead to an isozyme-specific elevation of the beta-2 isozyme in vascular tissues. Inoguchi et al., *Proc. Natl. Acad. Sci. USA* 89: 11059–11065 (1992). A diabetes-linked elevation of the beta isozyme in human platelets has been correlated with their altered response to agonists. Bastyr III, E. J. and Lu, J. *Diabetes* 42: (Suppl. 1) 97A (1993). The human vitamin D receptor has been shown to be selectively phosphorylated by protein kinase C beta. This phosphorylation has been linked to alterations in the functioning of the receptor. Hsieh et al., *Proc. Natl. Acad. Sci. USA* 88: 9315–9319 (1991); Hsieh et al., *J. Biol. Chem.* 268: 15118–15126 (1993). In addition, recent work has shown that the beta-2 isozyme is responsible for erythroleukemia cell proliferation while the alpha isozyme is involved in megakaryocyte differentiation in these same cells. Murray et al., *J. Biol. Chem.* 268: 15847–15853 (1993).

The ubiquitous nature of the protein kinase C Isozymes and their important roles in physiology provide incentives to produce highly selective PKC inhibitors. Given the evidence demonstrating linkage of certain isozymes to disease states, it is reasonable to assume that inhibitory compounds that are selective to one or two protein kinase C isozymes relative to the other PKC isozymes and other protein kinases are superior therapeutic agents. Such compounds demonstrate greater efficacy and lower toxicity py virtue of their specificity.

A class of N,N'-bridged bisindolylmaleimides has been disclosed in Heath et al., 08/413,735 (U.S. Pat. No. 5,552, 396), published on Jun. 14, 1995, as EP 0 657 458. A preferred compound in this N,N'-bridged series includes a compound of the Formula I:

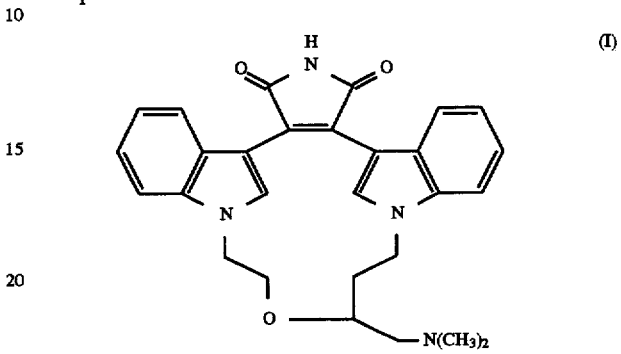

The present invention provides a novel, potent salt form of the compound of Formula I. Most unexpectedly, the claimed salt form has improved solubility and dramatically improved bioavailability to the patient. Furthermore, the salt is readily prepared and purified as a crystalline form. Thus, the claimed salt is more pharmaceutically elegant and a much improved therapeutic agent. The claimed salt is useful in treating conditions associated with diabetes mellitus and its complications, ischemia, inflammation, central nervous system disorders, cardiovascular disease, dermatological disease and cancer.

SUMMARY OF THE INVENTION

The invention provides a mesylate salt of a compound of Formula I. Thus, the invention provides a compound of the Formula Ia:

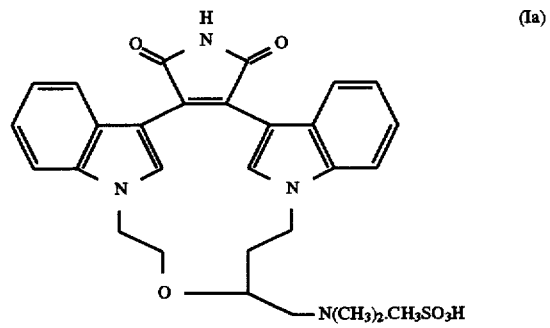

and solvates thereof.

One further aspect of the invention is a method of inhibiting Protein Kinase C, which comprises administering to a mammal in need of such treatment a pharmaceutically effective amount of a compound of the Formula Ia. The invention further provides methods for treating conditions that protein kinase C has demonstrated a role in the pathology, such as ischemia, inflammation, central nervous system disorders, cardiovascular disease, dermatological disease, and cancer, which comprise administering to a mammal in need of treatment a pharmaceutically effective amount of a compound of the Formula Ia.

This invention is particularly useful as a pharmaceutical and particularly in treating microvascular diabetic complications, particularly diabetic retinopathy, nephropathy, and neuropathy. Therefore, this invention further provides a method for treating diabetes mellitus and its complications, which comprises administering to a mammal in need of such treatment a pharmaceutically effective amount of a compound of Formula Ia.

A final aspect of the invention are pharmaceutical formulations comprising a compound of Formula Ia together with one or more pharmaceutically acceptable excipients, carriers, or diluents.

DETAILED DESCRIPTION AND PREFERRED EMBODIMENTS

For purposes of the present invention, as disclosed and claimed herein, the following terms and abbreviations are defined as follows:

The term "pharmaceutically effective amount", as used herein, represents an amount of compound that is capable of inhibiting PKC activity in mammals. The particular dose of the compound administered according to this invention will, of course, be determined by the particular circumstances surrounding the case, including the compound administered, the route of administration, the particular condition being treated, and similar considerations. The compound can be administered by a variety of routes including the oral, rectal, transdermal, subcutaneous, topical, intravenous, intramuscular or intranasal routes. Preferably, the compound is administered orally. For all indications, a typical daily dose will contain from about 0.01 mg/kg to about 20 mg/kg of the active compound of this invention. Preferred daily doses will be about 0.01 to about 10 mg/kg, more preferably below 1 mg/kg, and most preferably about 0.05 to about 0.5 mg/kg.

The term "treating," as used herein, describes the management and care of a patient for the purpose of combating the disease, condition, or disorder and includes the administration of a compound of present invention to prevent the onset of the symptoms or complications, alleviating the symptoms or complications, or eliminating the disease, condition, or disorder.

The term "total related substances" as used herein refers to the relative amounts of impurities in the final product. Impurities include, but are limited to, upstream reaction intermediates or undesired reaction by-products in the final product. Total related substances is a measure of purity.

As noted above, the invention provides compounds of the Formula Ia, which selectively inhibit protein kinase C:

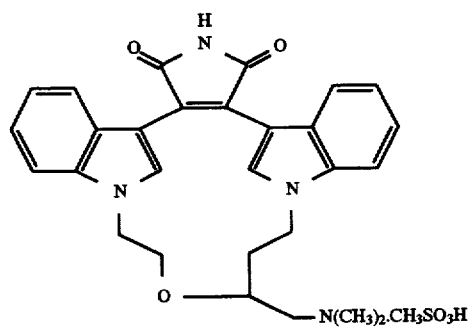

and solvates thereof.

The compound of Formula Ia can exist as solvates, such as with water (hydrate) methanol, ethanol, dimethylformamide, ethyl acetate and the like. Mixtures of such hydrates and solvates can also be prepared. The source of such hydrate and/or solvate can be from the solvent of crystallization, inherent in the solvent of preparation or crystallization, or adventitious to such solvent. Such hydrates and solvates are within the scope of the present invention. Preferably, the compounds of Formula Ia are prepared as the mono-hydrate or the trihydrate.

It is recognized that various stereoisomeric forms of the compounds of Formula Ia may exist. The preferred compounds of the present invention are of the Formula Ib and Ic:

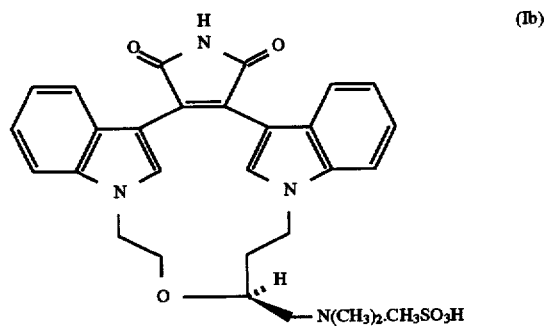

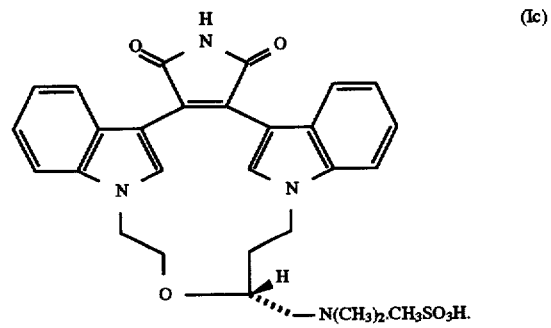

However, racemates and individual enantiomers and mixtures thereof form part of the present invention.

The preparation of the free base, Formula I, is described in Heath et al., 08/413,735 (U.S. Pat. No. 5,552,396), published on Jun. 14, 1995 as EP 0 657 458, herein incorporated by reference. Preferably, the compound is made as follows:

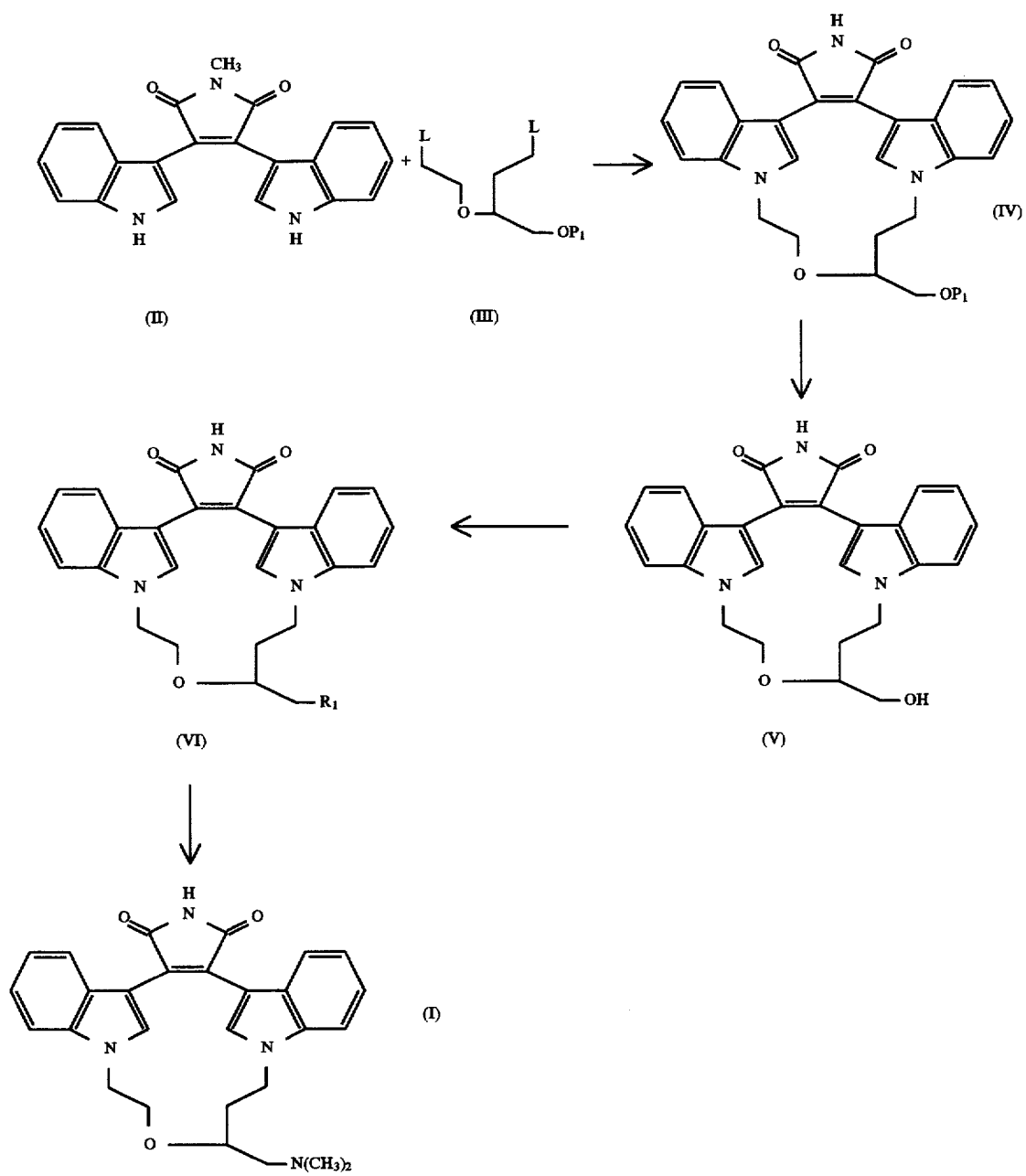

$R_1$ is OMesyl or Br. $P_1$ is a hydroxy protecting group, preferably tert-butyldiphenylsilyloxy (TBDPS), tert-butyldimethylsilyloxy (TBDMS), triphenylmethyl (trityl), mono- or di- methoxytrityl, or an alkyl or aryl ester. L is a good leaving group such as chloro, bromo, iodo, mesyl, tosyl, and the like. Preferably, L is O-mesyl or Br.

The reaction to form Compound IV is accomplished by any of the known methods of preparing N-substituted indoles. The reaction usually involves approximately equimolar amounts of reagents II and III, although other ratios, especially those wherein the alkylating reagent is in excess, are operative. The reaction is best carried out in a polar aprotic solvent employing an alkali metal salt or other such alkylation conditions as are appreciated in the art. Reaction conditions include the following: Potassium hexamethyldisilazide in dimethylformamide or tetrahydrofuran, sodium hydride in dimethylformamide. Preferably, the reaction is carried out under slow reverse addition with cesium carbonate in either acetonitrile, or dimethylformamide (DMF). The temperature of the reaction is preferably from about ambient temperature to about the reflux temperature of the reaction mixture.

Compound IV is converted to Compound V by techniques appreciated in the art for deprotecting a hydroxy. Compound V is conveniently converted to Compound VI by reacting Compound V with methanesulfonic anhydride and pyridine in THF or methylene chloride under nitrogen, or by reacting the alcohol with bromine in the presence of triphenyl phosphine or triphenyl phosphite and pyridine in methylene chloride, THF or acetonitrile or other suitable solvent. Compound VI is converted to the dimethylamine, Compound I, by reacting Compound VI with dimethylamine in a polar solvent such as DMF, THF/water, dimethylacetamide or other conditions appreciated in the art.

The claimed mesylate salt is prepared by reacting a compound of the Formula I with methanesulfonic acid in a non-reactive organic solvent, preferably a organic/water mixture, and most preferably water-acetone. Other solvents such as methanol, acetone, ethylacetate and mixtures thereof are operable. The ratio of solvent to water is not critical and generally determined by the solubility of the reagents. Preferred solvent to water ratios are generally from 0.1:1 to 100:1 solvent to water by volume. Preferably, the ratio is 1:1 to 20:1 and most preferably 5:1 to 10:1. The optimal ratio is dependent on the solvent selected and is preferably acetone at a 9:1 solvent to water ratio.

The reaction usually involves approximately equimolar amounts of the two reagents, although other ratios, especially those wherein the methanesulfonic acid is in excess, are operative. The rate of addition of methanesulfonic acid is not critical to the reaction and may be added rapidly (<5 minutes) or slowly over 6 or more hours. The reaction is carried out at temperatures ranging from 0° C. to reflux. The reaction is stirred until formation of the salt is complete, as determined by x-ray powder diffraction and can take from 5 minutes to 12 hours. The salts of the present invention are preferably and readily prepared as a crystalline form. The trihydrate form of the salt may be readily converted to the monohydrate upon drying or exposure to 20–60% relative humidity. The salt is substantially crystalline demonstrating a defined melting point, birefringence, and an X-ray diffraction pattern. Generally, the crystals have less than 10% amorphous solid and preferably less than 5% and most preferably less than 1% amorphous solid.

The mesylate salt is isolated by filtration or other separation techniques appreciated in the art directly from the reaction mixture in yields ranging from 50% to 100%. Recrystallization and other purification techniques known in the art may be used to further purify the salt if desired.

The following examples and preparations are provided merely to further illustrate the invention. The scope of the invention is not construed as merely consisting of the following examples. In the following examples and preparations, melting point, nuclear magnetic resonance spectra, mass spectra, high pressure liquid chromatography over silica gel, N,N-dimethylformamide, palladium on charcoal, tetrahydrofuran, and ethyl acetate are abbreviated M.Pt., NMR, MS, HPLC, DMF, Pd/C, THF, and EtOAc respectively. The terms "NMR" and "MS" indicate that the spectrum was consistent with the desired structure.

Preparation 1

3-(2-[(methylsulfonyl)oxy]ethoxy]-4-(tridhenylmethoxy)-1-butanol methane sulfonate Trityl chloride (175.2 g, 0.616 mole) was dissolved in 500 mL of $CH_2Cl_2$ under $N_2$. Triethylamine (71.9 g, 100 mL, 0.710 mole) was added and then R,S-glycidol (50.0 g, 0.648 mole) was added, and the reaction solution was heated to a gentle reflux (42° C.) for 4 hours. The reaction was cooled to room temperature and was extracted twice with 250 mL of an aqueous saturated solution of ammonium chloride and then 250 mL of brine. The aqueous layers were back-extracted with 100 mL of $CH_2Cl_2$ and the organic layer was dried ($MgSO_4$) and evaporated in vacuo to give and tritylglycidol as an oil that was recrystallized from ethanol to give 104.4 g (54%) of trityl-glycidol as a solid.

A 1M THF solution of vinylmagnesium bromide (50 mL, 50 mmol, 2.0 eq.) was cooled to −20° C. under $N_2$ and a catalytic amount of copper iodide was added (0.24 g, 1.26 mmol, 0.05 eq). The resultant mixture was stirred at −20° C. for 5 minutes and then a solution of trityl-glycidol (7.91 g, 25.0 mmol) in 40 mL of dry THF was added dropwise over 15 minutes at −20° C. The reaction mixture was stirred for 3 hours at −20° C. and then was allowed to warm to room temperature and stir for 15 minutes. The reaction was quenched by cooling the reaction mixture to −30° C. and 125 mL of an aqueous saturated solution of ammonium chloride was slowly added. The resultant mixture was extracted with 200 mL of ethyl acetate. The organic layer wan then extracted with an aqueous solution of 0.93 g (2.50 mmol, 0.1 eq.) of ethylenediaminetetraacetic acid, disodium salt dihydrate (EDTA) in 125 mL of deionized water to remove any metals. The aqueous layers were back extracted with 50 mL of ethyl acetate and the combined organic layers were washed with 100 mL of brine, dried ($MgSO_4$) and evaporated in vacuo to give an oil that was filtered through silica (76 g) using 1.2 L of 3/1 hexanes/ethyl acetate. The filtrate was evaporated in vacuo to give 9.07 g of 1-0-(triphenylmethyl)-2-hydroxy-pentanol as a light yellow colored oil (100%).

A 60% suspension of sodium hydride in mineral oil (6.13 g, 0.153 mol, 1.5 eq.) was suspended in 175 mL of dry THF was added at room temperature. The resultant mixture was stirred at room temperature for 1.5 hours and then 17.7 mL (0.204 mmol, 2.0 eq.) of freshly distilled allyl bromide was added via syringe. The reaction was heated to 45° C. for 1 hour. The reaction can be monitored by TLC or HPLC. The reaction mixture was cooled to 0° C. and 400 mL of an aqueous saturated solution of ammonium chloride was slowly added to quench the excess base. The resultant mixture was extracted with 800 mL of ethyl acetate and the organic layer was washed with 500 mL of water. The aqueous layers were back-extracted with 100 mL of ethyl acetate and the combined organic layers were washed with 200 mL of brine, dried ($MgSO_4$) and evaporated in vacuo to give 41.5 g (>100%) of 1,1',1"-[[[2-(2-propenyloxy)-4-pentenyl]oxy]methylidyne]tris[benzene] as a yellow oil.

1,1',1"-[[[2-(2-propenyloxy)-4-pentenyl]oxy]methylidyne]tris[benzene] (39.3 g, 0.102 mol) was dissolved in a solution of 390 mL of anhydrous methyl alcohol and 60 mL of $CH_2Cl_2$ and was cooled to −50° to −40° C. while bubbling $N_2$ through the viscous reaction solution. Ozone was then bubbled through the reaction mixture at −50° to −40° C. for 80 minutes until the reaction turned pale blue in color. The resultant reaction mixture was allowed to warm to 0° C. under $N_2$ and then a solution of sodium borohydride (23.15 g, 0.612 mole, 6 eq.) in 85 mL ethanol/ 85 mL water was slowly added to quench the reaction while keeping the reaction temperature below 10° C. The reaction was stirred in an ice bath for 30 minutes and then was allowed to warm to room temperature and stir overnight. The temperature rose to 31° C. upon warming. The reaction mixture was diluted with 400 mL of an aqueous saturated solution of ammonium chloride and was extracted with 800 mL of ethyl acetate. The organic layer was washed with 400 mL of water and the aqueous layers were back-extracted with 150 mL of ethyl acetate. The combined organic layer was washed with 200 mL of brine and was dried ($MgSO_4$) and evaporated in vacuo to give a cloudy oil. This oil was recrystallized from 2/1 hexanes/ethyl acetate in 3 crops to give 28.9 g of 3-(2-hydroxyethoxy)-4-(triphenylmethoxy)-1-butanol (72%).

3-(2-hydroxyethoxy)-4-(triphenylmethoxy)-1-butanol (14.0 g, 35.7 mmol) was dissolved in 140 mL of $CH_2Cl_2$, was cooled to 0° C. under $N_2$, and triethylamine (10.8 g, 14.9 mL, 0.107 mol, 3.0 eq.) was added. Methanesulfonyl chloride (11.0 g, 7.46 mL, 96.4 mmol, 2.7 eq.) was then added dropwise at <5° C. The resultant reaction mixture was diluted with additional $CH_2Cl_2$ (300 mL) and was washed with 200 mL of water and 200 mL of an aqueous saturated solution of ammonium chloride. The aqueous layers were back-extracted with 50 mL of $CH_2Cl_2$ and the combined organic layer was washed with 100 mL of brine and was dried ($MgSO_4$) and evaporated in vacuo to give 18.4 g (94%) of 3-(2-[(methylsulfonyl)oxy]ethoxy]-4-triphenylmethoxy)-1-butanol methane sulfonate as a white solid.

Preparation 2

(S)-Trityl Glycidol

Trityl chloride (2866 g, 10.3 mole) was dissolved in 7 L of $CH_2Cl_2$ under $N_2$. Triethylamine (1189 g, 1638 mL, 11.8 mole) was added, and then (R)-(+)-glycidol (795.0 g, 10.6 mole) was added using 1 L of $CH_2Cl_2$ as a rinse. The reaction solution was heated to a gentle reflux (42° C.) for 3–4 hours. The reaction was cooled to room temperature and then 3 L of brine was added. The organic layer was dried (600 g $Na_2SO_4$) and evaporated in vacuo to give the titled compound as an oil that was recrystallized from ethanol to give 2354 g (70%) of the titled compound as a solid.

Preparation 3

(S)-3-[2-[(methylsulfonyl)oxy]ethoxy]-4-(triphenylmethoxy)-1-butanol methanesulfonate A 1M THF solution of vinylmagnesium bromide (5.76 L, 5.76 mole, 1.96 eq.) was cooled to −20° C. under $N_2$ and a catalytic amount of copper iodide was added (28.2 g, 0.148 mole, 0.05 eq.). The resultant mixture was stirred at −20° C. for 5 minutes, and then a solution of (S)-Trityl-glycidol (929.0 g, 2.94 mole) in 3.2 L of dry THF was added dropwise over 1.5 hours at −20° C. The reaction mixture was stirred for 1 hour at −20° C. The reaction was quenched by cooling the reaction mixture to −30° C. and 5 L of an aqueous saturated solution of ammonium chloride was slowly added. The organic layer was then extracted twice with 1 L a 10% wt./volume solution of ethylenediaminetetraacetic acid, disodium salt dihydrate (EDTA) to remove any metals. The organic layer was washed with 2 L of brine, dried ($MgSO_4$) and evaporated in vacuo to give 1061 g (96%) of (S)-1-0-triphenylmethyl-4-hydroxypentanol as an oil.

A 60% suspension of sodium hydride in mineral oil (268.9 g, 6.72 mole, 1.5 eq.) was suspended in 2.8 L of dry THF under $N_2$ and a solution (S)-1-0-triphenylmethyl-4-hydroxypentanol (1543 g, 4.48 mole) in 5.6 L of dry THF was added at room temperature. The resultant mixture was stirred at room temperature for 1.5 hours and then 770 mL (8.89 mole, 2.0 eq.) of freshly distilled allyl bromide was added over 20 minutes. The reaction was heated to 45° C. for 1–2 hours. The reaction mixture was cooled to 15°–20° C. and 2 L of an aqueous saturated solution of ammonium chloride was slowly added to quench the excess base. The resultant mixture was diluted with 1 L of ethyl acetate and 1 L of water and the organic layer was isolated. The aqueous layer was back-extracted with 500 mL of ethyl acetate and the combined organic layers were dried ($MgSO_4$) and evaporated in vacuo to give 1867 g (98%) of (S)-1,1',1"-[[[2-(2-propenyloxy)-4-pentenyl]oxy]methylidyne]tris[benzene] as a yellow oil.

(S) -1,1', 1"-[[[2- (2-propenyloxy) -4-pentenyl]oxy] methylidyne]tris[benzene] (1281 g, 3.33 mole) was dissolved in a solution of 4 L of anhydrous methyl alcohol and 3.6 L of $CH_2Cl_2$ and was cooled to −50° to −40° C. while bubbling $N_2$ through the viscous reaction solution. Sudan III indicator was added to the reaction and ozone was bubbled through the reaction mixture at −50° to −35° C. for 13 hours until the reaction turned from a peach color to a light green/yellow color. The resultant reaction mixture was allowed to warm to 0° C. under $N_2$ and was then slowly added over 40 minutes to a solution of sodium borohydride (754 g, 19.9 mole, 6 eq.) in 2.5 L ethanol/ 2.5 L water while keeping the reaction temperature below 30° C. The reaction was then allowed to stir at room temperature overnight. The reaction can be monitored by HPLC. The reaction mixture was cooled to 10°–15° C. and was slowly added to 4 L of an aqueous saturated solution of ammonium chloride at <20° C. The quenched reaction mixture was then filtered and the solids washed with 3 L of $CH_2Cl_2$. The organic layer was isolated and was washed with 3 L of an aqueous saturated solution of ammonium chloride and the aqueous layers were back-extracted with 1 L of $CH_2Cl_2$. The combined organic layer was dried ($MgSO_4$) and evaporated in vacuo to give a 1361 g (>100%) of (S)-3-(2-hydroxyethoxy)-4-(tripenylmethoxy)-1-butanol as an oil.

(S)-3-(2-hydroxyethoxy)-4-(tripenylmethoxy)-1-butanol (500 g, 1.27 mole) was dissolved in 4.8 L of $CH_2Cl_2$, was cooled to 0° C. under $N_2$, and triethylamine (386.4 g, 532 mL, 3.81 mole, 3.0 eq.) was added. Methanesulfonyl chloride (396.3 g, 268 mL, 3.46 mole, 2.7 eq.) was then added dropwise over 30 minutes at <5° C. The resultant reaction mixture was stirred at 0° to 5° C. for 1–2 hours and was monitored by HPLC. The reaction mixture was diluted with additional $CH_2Cl_2$ and was washed twice with 2 L of water and 2 L of an aqueous saturated solution of ammonium chloride. The aqueous layers were back-extracted with 1 L of $CH_2Cl_2$ and the combined organic layer was dried ($MgSO_4$) and evaporated in vacuo to give a crude solid that was recrystallized from 1/1 heptane/ethyl acetate to give 615 g (88%) of (S)-3-[2-[(methylsulfonyl)oxy]ethoxy]-4-(triphenylmethoxy)-1-butanol methane sulfonate in three crops as a solid. NMR. MS.

Preparation 4

3-[2-iodoethoxy]-4-(tripenylmethoxy)-1-iodobutane

A solution of 3-(2-[(methylsulfonyl)oxy]ethoxy]-4-triphenylmethoxy)-1-butanol methane sulfonate (5.0 g, 9.10 mmol) in 500 mL of reagent grade acetone was treated with sodium bicarbonate (0.0770 g, 0910 mmol, 0.1 eq.) and sodium iodide (34.2 g, 0.228 mol. 25 eq.). The resultant mixture was stirred at 50° C. under $N_2$ for approximately 16 hours. This reaction can be monitored by HPLC. The acetone was removed from the reaction mixture in vacuo and the resultant solid was extracted into a 300 mL of ethyl acetate/200 mL water mixture. The organic layer was washed with 200 mL more water and the combined aqueous layer was back-extracted with 100 mL of additional ethyl acetate. The combined organic layer was washed with 200 mL of a 10% aqueous solution of sodium sulfite (this wash removed the yellow color), 100 mL of brine, was dried ($MgSO_4$), and was evaporated in vacuo to give 5.45 g (98%) of 3-[2-iodoethoxy]-4-(tripenylmethoxy-iodobutone as a clear oil. MS. NMR.

Preparation 5

(S)-10, 11, 14, 15-tetrahydro-13-[methanesulfonyloxy (methyl)]-4,9: 16, 21-dimetheno-1H, 13H-dibenzo[E,K] pyrrolo[3,4-H],[3,4,13]oxadiazacyclohexadecine-1,3-dione 3,4-(bis)-(1H-indol-3-yl)-N-methylmalemide (10.04 g, 29.4 mmol) and (S)-3-(2-iodoethoxy)-4-(tert-butyl diphenylsilyloxy)-1-iodobutane (17.9 g, 29.4 mmol) were combined and dissolved in anhydrous DMF (80 mL). The solution was added via syringe pump addition over 72 hours to a suspension of cesium carbonate (38.3 g, 118 mmol) in anhydrous DMF (1.7 L) at 50° C. under $N_2$. The DMF was removed in vacuo. The residue was partitioned between $CHCl_3$/1N HCl. The acidic layer was back-extracted with chloroform and ethyl acetate. The combined organic layers were washed with 1N HCl (1×), water (2×), brine (2×), dried over $Na_2SO_4$, and reduced to give a magenta solid. The crude reaction mixture was used without further purification.

The crude reaction mixture was suspended in ethanol (700 mL) and treated with 5N KOH (800 mL). The reaction temperature was raised to 80° C. After 72 hours the ethanol was removed in vacuo; the aqueous suspension was cooled to 0° C., and acidified with 5N HCl. The violet precipitate was collected and passed through a silica plug eluting with ethyl acetate. The eluant was concentrated to yield 8.7 g of the partially silylated maleimide as a magenta solid that was carried on to the next reaction without further purification.

To a DMF (1 L) solution of the above anhydride (8.7 g, 19.7 mmol) was added 1,1,1,3,3,3-hexamethyldisilazane (41.6 mL, 197 mmol) and methanol (4 mL, 98.5 mmol) under nitrogen at ambient temperature. After 40 hours, the reaction was concentrated in vacuo , a 2:1 (v/v) MeCN/1N HCl solution (100 mL) was added. The residue was stirred for one hour. The organic solvent was removed; and the aqueous suspension was extracted with ethyl acetate. The solvents were removed to yield 8.9 g of maleimide that was used without further purification.

To a $CH_2Cl_2$ (800 mL) suspension of the above maleimide (8.9 g, 20 mmol) under nitrogen at ambient temperature was added pyridine (4.85 mL, 60 mmol) and a slight excess of methanesulfonic anhydride (4.21 g, 24 mmol). After 16 hours the reaction mixture was washed with 0.1N HCl , brine, and the organic layer was concentrated. The residue was passed through a plug of silica eluting with a slow gradient of 0–10% MeCN in $CH_2Cl_2$. The eluant fraction containing the desired mesylate was concentrated to yield 2.8 g of the titled compound as a magenta solid. Overall yield from the diiodide is 18%. MS.

Preparation 6

(S)-13-[(dimethylamino)methyl]-10,11,14,15,-tertrahydro-4,9:16-21-dimetheno-1H, 13H-dibenzo[E,K]pyrrolo[3,4-H][1,4,13]oxadiazacyclohexadecine-1,3(2H)-dione 2,3-Bis-(1H-indol-3-yl)-N-methylmaleimide (114.7 g, 0.336 mole) and (S)-3-[2-[(methylsulfonyl)oxy]ethoxy]-4-(triphenylmethoxy)-1-butanol methane sulfonate (220.0 g, 0.401 mole, 1.2 eq.) were dissolved in 4.3 L of DMF. This solution of reagents was then added slowly over 70 hours (at approximately 1 mL/min.) to a 50° C. slurry of cesium carbonate (437.8 g, 1.34 mole, 4.0 eq.) in 7 L of DMF. After 70–72 hours the reaction was cooled and filtered, and the DMF was removed in vacuo to give a residue that was dissolved in 4.6 L of $CH_2Cl_2$. The organic layer was extracted with 1.15 L of aqueous 1N HCl and then with 4.6 L of brine. The combined aqueous layers were back-extracted with 1.1 L of $CH_2Cl_2$. The combined organic layer was dried ($Na_2SO_4$) and filtered. Most of the solvent was removed in vacuo, and the resultant solution was filtered through 2 Kg of silica gel using 4–5 gallons of additional $CH_2Cl_2$ to remove baseline material. The solvent was removed in vacuo and the resultant purple colored solid triturated in 7 volumes of acetonitrile (based on weight of crude (S)-10,11,14,15-tetrahydro-2-methyl-13-[(triphenylmethoxy) methyl]-4,9:16,21-dimetheno-1H, 13H-dibenzo[E,K]pyrrolo[3,4-H][1,4,13] oxadiazacyclohexadecine-1,3(2H)-dione to give 150.2 g (57%) of (S)-10,11,14,15-tetrahydro-2-methyl-13-[(triphenylmethoxy) methyl]-4,9:16,21-dimetheno-1H,13H-dibenzo[E,K]pyrrolo[3,4-H][1,4,13] oxadiazacyclohexadecine-1,3(2H)-dione after drying (89% pure by HPLC vs. standard).

(S)-10,11,14,15-tetrahydro-2-methyl-13-[(triphenylmethoxy) methyl]-4,9:16,21-dimetheno-1H,13H-dibenzo[E,K]pyrrolo[3,4-H][1,4,13] oxadiazacyclohexadecine-1,3(2H)-dione (32.7 g, 46.9 mmol) was suspended in 1.6 L of ethanol and 1.6 L of aqueous 10N KOH. The resultant mixture was heated to a gentle reflux (78° C.) for 19 hours. Most of the solids dissolved upon reaching reflux. The reaction solution was cooled to 10° to 15° C. and aqueous 10N HCl (1.2 L) was slowly added at <15° C. to adjust the acidity to pH=1. A red slurry developed upon acidification. The reaction mixture was diluted with 500 mL of $CH_2Cl_2$ and was stirred for 20 minutes and filtered to remove most of the salts. The salts were washed with additional $CH_2Cl_2$ (1.5 L), and the filtrate was extracted twice with 1 L of water. The combined aqueous layers were back-extracted with 1 L of $CH_2Cl_2$, and the organic layer was dried ($MgSO_4$). The solvent was removed in vacuo to give 36.0 g (>100%) ( S)-10,11,14,15-tetrahydro-13-[(triphenylmethoxy) methyl]-4,9:16,21-dimetheno-13H-dibenzo[E,K]furo[3,4-H][1,4,13] oxadiazacyclohexadecine-1,3-dione as a purple solid (80% pure by HPLC area).

(S)-10,11,14,15-tetrahydro-13-[(triphenylmethoxy) methyl]-4,9:16,21-dimetheno-13H-dibenzo [E,K]furo[3,4-H][1,4,13]oxadiazacyclohexadecine-1,3-dione (36.0 g, assume 46.9 mmol) was dissolved in 320 mL of dry DMF under $N_2$ and was treated with a pre-mixed solution of 1,1,1,3,3,3-hexamethyldisilazane (99 mL, 75.7 g, 0.469 mol, 10 eq.) and methanol (9.5 mL, 7.51 g, 0.235 mol. 5 eq.). The resultant solution was heated at 45° C. for 7 hours. The reaction can be monitored by HPLC. Most of the DMF was removed in vacuo, and the resultant residue was extracted into 200 mL of ethyl acetate and washed with 200 mL of water and twice with 100 mL of an aqueous 5% LiCl solution. The aqueous layers were back-extracted with 100 mL of ethyl acetate. The combined organic layer was washed with 200 mL of a saturated aqueous solution of ammonium chloride. The combined organic layer was dried ($MgSO_4$) and evaporated in vacuo to give 35.9 g (>100%) of the crude ( S)-10,11,14,15-tetrahydro-13-[(triphenylmethoxy)methyl]-4,9:16,21-dimeth-eno-1H; 13H-dibenzo[E,K]pyrrolo[3,4-H][1,4,13] oxadiazacyclohexadecine-1,3(2H)-dione as a purple solid.

(S)-10,11,14,15-tetrahydro-13-[(triphenylmethoxy) methyl]-4,9:16,21-dimeth-eno-1H; 13H-dibenzo [E,K] pyrrolo[3,4-H][1,4,13]oxadiazacyclohexadecine-1,3 (2H)-dione (34.0, assume 46.8 mmol) was dissolved in 350 mL of $CH_2Cl_2$ and was cooled to −25° C. under $N_2$. Anhydrous HCl gas was bubbled into the reaction solution for approximately 1–2 minutes at <0° C. The resultant slurry was allowed to warm to room temperature and stir for 1 hour. The reaction can be monitored by HPLC. The slurry was filtered and the solids were washed with 200 mL of $CH_2Cl_2$. The solid was dried in a vacuum oven at 50° C. to give 18.6 g (90%) (S)-10,11,14,15-tetrahydro-13-(hydroxymethyl)-4, 9:16,21-dimetheno-1H,13H-dibenzo[E,K]pyrrolo[3,4-H][1,4,13]oxadiazacyclohexadecine-1,3(2H)-dione as a purple solid (93% pure by HPLC area).

A suspension of (S)-10,11,14,15-tetrahydro-13-(hydroxymethyl)-4,9:16,21-dimetheno-1H, 13H-dibenzo[E, K]Pyrrolo[3,4-H][1,4,13]oxadiazacyclohexadecine-1,3(2H)-dione (18.2 g, 41.2 mmol) in 900 mL of THF was treated with pyridine (9.78 g, 10.0 mL, 0.124 mmol, 3 eq.) and methanesulfonic anhydride (14.3 g, 80.4 mmol, 2 eq.) and was heated to reflux (67° C.) for 16 hours under $N_2$. This reaction can be monitored by HPLC. The reaction was then cooled and diluted with 600 mL of ethyl acetate and extracted twice with 300 mL of 1N HCl and once with 600 mL of water. The aqueous layers were back-extracted with 300 mL of ethyl acetate and the organic layer dried ($MgSO_4$). The solvent was removed in vacuo to give 19.0 of (S)-10,11,14,15-tetrahydro-13-[[methylsulfonyl)oxy] methyl]-4,9:16,21-dimetheno-1H, 13H-dibenzo[[E,K] pyrrolo[3,4-H][1,4,13]oxadiazacyclohexadecine-1,3(2H)-dione that was triturated in 190 mL of hot (40° C.) $CH_2Cl_2$ and was filtered hot and washed with 100 mL of additional room temperature $CH_2Cl_2$ to give 17.3 g (81%) of (S)-10, 11,14,15-tetrahydro-13-[[methylsulfonyl) oxy]methyl]-4, 9:16,21-dimetheno-1H, 13H-dibenzo[[E,K]pyrrolo[3,4-H] [1,4,13]oxadiazacyclohexadecine-1,3(2H)-dione as a purple solid (96% pure by HPLC area).

(S)-10,11,14,15-tetrahydro-13-[[methylsulfonyl) oxy] methyl]-4,9:16,21-dimetheno-1H,13H-dibenzo[[E,K] pyrrolo[3,4-H][1,4,13]oxadiazacyclohexadecine-1,3 (2H)-dione (9.50 g, 18.3 mmol) was dissolved in 475 mL of THF and 172 mL of a 40% aqueous solution of dimethylamine (0.173 mole, 75 eq.) was added, the resultant solution was heated at 65° C. in a sealed reactor (8–10 psi.) for 19 hours. The reaction was cooled and diluted with 900 mL of ethyl acetate and the organic layer was extracted twice with 450 mL of water and once with 200 mL of brine. The aqueous layers were back-extracted with 250 mL of additional ethyl acetate and the organic layer was dried ($MgSO_4$), and the solvent was removed in vacuo to give 7.82 g of (S)-13-[dimethylamino)methyl]-10,11,14,15-tetrahydro-4,9:16,21-dimetheno-1H, 13H-dibenzo[E,K]pyrrolo[3,4-H][1,4,13] oxadiazacyclohexadecine-1,3(2H)-dione (91%).

EXAMPLE 1

Mesylate Salt (S)-13-[(dimethylamino)methyl]-10,11,14,15-tetrahydro-4,9:16,21-dimetheno-1H, 13H-dibenzo[E,K]pyrrolo[3,4-H] [1,4,13]oxadiazacyclohexadecine-1,3(2H)-dione (3.0 g, 6.4 mmol) was suspended in 90 mL of reagent grade acetone. Methanesulfonic acid (0.62 g, 1 eq) was dissolved in 10 mL of deionized water and added to the base/acetone slurry. The resultant reddish-orange slurry was stirred and filtered using 25 mL of acetone as a rinse to give 2.92 g (81%) of mesylate salt after drying. All procedures, including rinses were performed at room temperature.

EXAMPLE 2

Mono/Hydrochloride Salt

The monohydrochloride salt of (S)-13-[dimethylamino) methyl]-10,11,14,15-tetrahydro-4,9:16,21-dimetheno-1H, 13H-dibenzo[E,K]pyrrolo[3,4-H][1,4,13] oxadiazacyclohexadecine-1,3(2H)-dione was prepared by suspending the base (3.0 g, 6.4 mmol) in 120 mL (1 eq) of methanol. Aqueous 1N HCl was added. The resultant mixture was stirred for approximately 16 hours and filtered using 25 mL of methanol as a rinse. The resultant salt was dried in a vacuum oven overnight at 50° C. to give 2.65 g (82%) of HCl salt. All procedures, including rinses, were performed at room temperature.

EXAMPLES 3–8

Hydrochloride, Sulfate, Tartrate, Succinate, Acetate and Phosphate Salts

The hydrochloride, sulfate, tartrate, succinate, acetate and phosphate salts were prepared utilizing a methanol/water solvent mixture by techniques appreciated in the art. Each of the salts were prepared by adding a water solution of the acid to a methanol suspension of (S)-13-[dimethylamino)methyl] -10,11,14,15-tetrahydro-4,9:16,21-dimetheno-1H, 13H-dibenzo[E,K]pyrrolo[3,4-H][1,4,13] oxadiazacyclohexadecine-1,3(2H)-dione.

Most unexpectedly, the claimed salt form has improved solubility and, most significantly, dramatically improved bioavailability to the patient. The salt is readily prepared in crystalline form and results in a greater reduction of impurities. The following examples provide a comparative analysis demonstrating the unexpected and superior properties of the claimed salt.

EXAMPLE 9

Comparison of Yield, Total Related Substances and Residual Solvents

Total related substances refers to the relative amounts of impurities in the final product and is thus a measure of the purity. For the salts prepared the highest yield, 82%, was observed during preparation of the sulfate (Table I), with the lowest yield, 52%, being obtained for the succinate. Although the total related substances (TRS) were reduced in the preparation of each of the salts, the largest reduction of 5.26% was observed during preparation of the mesylate salt. The hydrochloride salt was the only salt that contained residual methanol (0.62 wt. %) after drying at 50° C. in a vacuum oven for approximately 16 hours. The succinate, acetate and phosphate contained 0.18 to 1.32% THF by GC assay which is presumably left in the salts from the penultimate step in the synthesis which was carried out in an aqueous THF.

TABLE I

Yield, % TRS and % Residual Solvent Results for Different Salt Forms.

| Salt | Yield (%) | TRS (%, HPLC)[a] | Residual Solvents, (%)[b] |
|---|---|---|---|
| HCl | 69 | 9.12 | 0.62 MeOH |
| Sulfate | 82 | 7.28 | none |
| Tartrate | 77 | 8.95 | none |
| Mesylate | 63 | 4.72 | none |
| Succinate[c] | 52 | 7.86 | 1.32 THF |
| Acetate[c] | 68 | 8.05 | 1.12 THF |
| Phosphate[d] | 79 | 6.28 | 0.18 THF |

[a]The free base utilized to prepare these salts had 9.98% total related substances.
[b]Assay limit of detection was 0.1% (1000 ppm). All salts were prepared in methanol/water and dried for approximately 16 hours in a vacuum oven at 50° C. before assay.
[c]Succinate and acetate were not fully titrated under conditions for preparation as determined by X-ray powder diffraction.
[d]Phosphate was partially titrated as determined by X-ray powder diffraction.

EXAMPLE 10

Comparison by X-Ray Diffraction

The salts were also compared by polarizing microscopy to determine crystallinity (birefringence). Powder X-Ray diffraction indicated that only the hydrochloride, mesylate, succinate and acetate salts were crystalline and resulted in unique X-ray patterns. The succinate and acetate X-ray powder patterns were very similar to each other and were shown to correlate with the free base pattern. The sulfate, tartrate, and phosphate salts were poorly crystalline having significant amorphous character. Crystalline salts are preferred due to ease of purification and subsequently handling.

EXAMPLE 11

Comparison of Solubility

The aqueous solubility of each salt was determined by UV analysis (Table II) and compared. Most unexpectedly, the mesylate salt has the greatest aqueous solubility, 1.76 mg/mL. The solubility of the mesylate is significantly higher than the other salts. The data in Table II demonstrate that the claimed salt is six times more soluble in water than the most common pharmaceutically acceptable salt, the hydrochloride salt (0.268 mg/mL). Subsequent studies consistently demonstrate a two to six fold increase in solubility. The high pH observed with the succinate and acetate salt indicated the presence of untitrated free base.

TABLE II

| | Aqueous Solubility. | | |
|---|---|---|---|
| Salt | Solubility (μg salt/mL H$_2$O) | Solubility (μg base/mL H$_2$O) | pH (saturated aq Solution) |
| HCl | 268 | 249 | 4.98 |
| Sulfate | 14 | 12 | 2.57 |
| Mesylate | 1760 | 1460 | 4.69 |
| Succinate | 0.5 | 0.4 | 7.72 |
| Tartrate | 71 | 54 | 3.77 |
| Acetate | 1 | 0.9 | 7.80 |
| Phosphate | 736 | 609 | 3.78 |

The aqueous solubility of the mesylate salt is very pH dependent in that optimal solubility is observed at pH 4.0 to 5.0 and most preferably pH 4.5 (2.25 mg/mL). The solubility drops markedly at either higher or lower pH. In addition to the pH dependence of the solubility, the aqueous solubility of the mesylate salt drops markedly with the addition of chloride in the form of sodium chloride due to the formation of the HCl salt.

EXAMPLE 12

Comparison of Thermograyometric Analysis (TGA), Differential Scanning Calorimetry (DSC), and Mettler Hot Stage Microscopy Each salt was analyzed by TGA, DSC and Mettler hot stage microscopy and compared (Table III). The salts displayed a weight loss of 0.73 to 5.50% when heated from 20° to 100° C. The sulfate, tartrate and phosphate salts showed the greatest weight loss at 5.50% each. When the salts were heated from 100° to 200° C., the hydrochloride, succinate and acetate salts were the only salts that exhibited further weight loss. DSC analysis indicated that the mesylate salt produced a sharp endotherm melt peak at 261.6° C. The sulfate salt displayed a somewhat broad endotherm at 267.4° C. The hydrochloride, succinate, tartrate, acetate and phosphate salts did not exhibit a melting endotherm by DSC. The succinate, acetate, and phosphate displayed DSC exotherms at approximately 245° C. The samples were also examined by hot stage microscopy using a Mettler hot stage. The hydrochloride salt did not show any real melting up to a temperature of 300° C. The rest of the salts examined showed signs of liquidification at temperatures of 215° to 270° C.

TABLE III

| | TGA, DSC and Hot Stage Microscopy Results. | | | |
|---|---|---|---|---|
| Salt | TGA (% wt loss) 20–100° C. | TGA (% wt loss) 100–200° C. | DSC Endotherm max (°C.) | Hot Stage Microsc. (°C.) |
| HCl | 1.42 | 0.9 | no MP | no MP |
| Sulfate | 5.50 | — | 267.4 | 260–270 |
| Mesylate | 3.97 | — | 261.6 | 230–264 |
| Succinate | 0.73 | 1.90 | no MP | 230–270 |
| Tartrate | 5.50 | — | no MP | 215–255 |
| Acetate | 0.77 | 1.44 | no MP | 245–265 |
| Phosphate | 5.50 | — | no MP | 230–250 |

EXAMPLE 13

Comparison of Hygroscopicity

The salts were examined for hygroscopicity at relative humidities (RH) of 27%, 35%, 65% and 80% and are depicted in Table IV. The samples were subjected to vacuum initially to establish a reference point for the RH data. The amount of water contained in each salt was also determined by Karl-Fisher (coulometric).

TABLE IV

| | Hygroscopicity and Karl-Fisher (K. F.) Results. | | | | | | |
|---|---|---|---|---|---|---|---|
| Salt | Hygroscopicity (wt % initial) | Vacuum | RH 27% | RH 35% | RH 65% | RH 80% | K. F. (%) |
| HCl | 100 | 98.7 | 98.2 | 99.3 | 100.4 | 100.6 | 1.3 |
| Sulfate | 100 | 98.9 | 98.4 | 99.8 | 100.9 | 101.9 | 4.9 |
| Mesylate | 100 | 99.0 | 98.5 | 99.4 | 100.7 | 104.4 | 3.6 |
| Succinate | 100 | 99.3 | 98.5 | 99.1 | 100.0 | 100.5 | 0.2 |
| Tartrate | 100 | 97.9 | 98.2 | 101.3 | 103.8 | 105.4 | 5.1 |
| Acetate | 100 | 99.4 | 98.6 | 99.2 | 100.2 | 100.6 | 0.3 |
| Phosphate | 100 | 98.2 | 98.6 | 102.6 | 105.5 | 106.6 | 4.6 |

The salts gained from 1.2 to 8.4% weight when comparing the weights from exposure to vacuum to exposure to 80% RH. The phosphate salt was the most hygroscopic followed by the tartrate salt, mesylate, sulfate, acetate, hydrochloride and succinate. The Karl-Fisher data matched the hygroscopicity data fairly well in that the tartrate, sulfate, phosphate and mesylate salts contained the most water.

EXAMPLE 14

Solvents for Salt Preparation

The mesylate salt was prepared in methanol/water, 100% acetone, 9:1 acetone/water, 3:1 acetone/water and 1:1 acetone/water. The base that was utilized to prepare these salts contained 9.98% total related substances. The yields, and total related substances obtained for each of these salts are listed in Table V. For comparison data for the HCl salt are included. The designation of N.A. in Table V indicates that the data are not available.

TABLE V

Yield and % TRS for HCl and Mesylate Salts.

| Salt | Solvent | Yield % | TRS (%, HPLC)[a] | Residual Solv. (%)[c] |
|---|---|---|---|---|
| HCl | 30:1 MeOH/H$_2$O | 69 | 9.12[a] | 0.62 MeOH |
| HCl | 9:1 Acetone/H$_2$O | 83 | 4.73[a] | N. A. |
| HCl | 20:1 MeOH/H$_2$O | 82 | 2.23[b] | 0.05 MeOH |
| Mesylate | 7:1 MeOH/H$_2$O | 63 | 4.72[a] | none |
| Mesylate | Acetone | 85 | 9.80[a] | N. A. |
| Mesylate | 9:1 Acetone/H$_2$O | 73 | 2.00[a] | N. A. |
| Mesylate | 5:1 Acetone/H$_2$O | 39 | 0.69[a] | N. A. |
| Mesylate | 1:1 Acetone/H$_2$O | 29 | 4.12[a] | N. A. |
| Mesylate | 9:1 Acetone/H$_2$O | 81 | 0.91[b] | 0.69 Acetone |

[a]The base utilized to prepare these salts had 9.98% total related substances.
[b]The base utilized to prepare these salts had 7.03% total related substances.
[c]Assay limit of detection was 0.1% (1000 ppm).

The mesylate salt prepared from 5:1 acetone/water had 0.7% total related substances, a reduction of 9.3% from the TRS of the free base, however the yield was low at 39%. The yield increased to 73%, with 2.0% TRS if 9.1 acetone water was utilized. The TRS of the hydrochloride salt was also reduced to 4.7%, a 5.3% reduction, however 2.4% of an unknown related substance was present. The ability to produce the claimed salts with significantly reduced impurities (TRS) results in a more efficient preparation and avoids costly downstream purification.

Because the hydrochloride salt is the most common pharmaceutical salt and is specifically disclosed in Heath et al., EP 0 657 458, published on Jun. 14, 1995 (Example 5), a biological comparison of the mesylate and HCl salt was carried out. Most unexpectedly, the claimed mesylate salt is significantly more bioavailable than the HCl salt. The bioavailability of the salt forms was measured in four Male Beagle Dogs by orally administering a single 20 mg/kg dose of the HCl and the claimed mesylate salt in a 10% acacia suspension. One week washout period was allowed between doses. Doses were administered in a cross-over design (2 dogs/salt/study dog). The plasma concentration of the active compound as well as an active metabolite was monitored. Higher plasma concentrations of (S)-13-[dimethylamino) methyl]-10,11,14,15-tetrahydro-4,9:16,21-dimetheno-1H, 13H-dibenzo [E, K]pyrrolo [3,4-H][1,4,13] oxadiazacyclohexadecine-1,3 (2H)-dione and the metabolite were achieved in each dog following an oral dose of the claimed mesylate salt than an equivalent dose of the HCl salt. The mean maximum plasma concentration ($C_{max}$±error) following the administration of the HCl salt was 400±142 ng/mL (compound) and 862±255 ng/mL (metabolite). The mean maximum plasma concentration ($C_{max}$±error) following the administration of the claimed mesylate salt was 896±243 ng/mL (compound) and 2455±930 ng/mL (metabolite). This represents an approximately 260% increase in plasma concentration of the compound and the metabolite.

The plasma concentration of the compound as well as the metabolite was also plotted as a function of time during the study. The ratio of the area under the concentration curve (AUC) represents a measure of bioavailability of the compound to the patient. The AUC ratio for the HCl salt and the claimed mesylate was calculated and is depicted in Table VI.

TABLE VI

AUC Ratios from a Single Oral 20 mg/kg Dose Administered as the HCl and Mesylate Salts.

| | AUC Ratios | |
|---|---|---|
| Dog # | Metabolite Mesylate:HCl | Compound Mesylate:HCl |
| 1 | 2.77 | 3.89 |
| 2 | 2.97 | 1.62 |
| 3 | 2.02 | 2.14 |
| 4 | 2.74 | 2.56 |
| Mean | 2.62 | 2.55 |
| Std. Error | 0.21 | 0.49 |

Most unexpectedly, the data in Table VI demonstrate that the mesylate salt is 2.58 times more bioavailable than the HCl salt. This significant increase in bioavailability allows a lower dose to be administered to a patient to get the same pharmaceutical effect. Thus, the exposure to the patient is minimized. Additionally, the lower unit dosage form lowers the cost of the compound and reduces the amount of compound required for manufacture. Therefore, the dose of the mesylate salt of the present invention is predicted to be 0.5 mg/kg/day to 0.25 mg/kg/day, more preferably 0.1 to 0.2 mg/kg/day. This dose is substantially lower than the dose of the HCl salt which yields the same blood level.

A summary of the physical data for the seven salts indicates that the mesylate salt has significantly improved physical properties of the salts studied and disclosed in Heath et al., EP 0 657 458. Most significantly, a comparison of the bioavailability of the claimed salt and the HCl salt demonstrates the claimed mesylate salts are dramatically improved therapeutic agents. Thus, the advantages of the claimed mesylate salts include:

(1) high aqueous solubility;
(2) large reduction in HPLC total related substances;
(3) no residual solvents by GC assay;
(4) crystalline by X-Ray powder diffraction and polarizing microscopy;
(5) a sharp melting point by DSC; and
(6) greater than 2.5 times the bioavailability of the HCl salt.

As previously stated, the compound of the present invention are active as selective Protein Kinase C inhibitors. The activity of compound is disclosed in Heath et al., EP 0 657 458, published on Jun. 14, 1995. The activity was determined in the Calcium Calmodulin Dependent Protein Kinase Assay, Casein Protein Kinase II assay, cAMP-Dependent Protein Kinase Catalytic Subunit assay and the Protein-Tyrosine Kinase assay. The mesylate salt was found to be active and isozyme selective in the these assays at an IC$_{50}$ value of less than 10 µM. Compounds with this demonstrated pharmacological activity are useful in the treatment of conditions in which protein kinase C has demonstrated a role in the pathology. Conditions recognized in the art include: diabetes mellitus and its complications (including retinopathy, neuropathy and nephropathy), ischemia, inflammation, central nervous system disorders, cardiovascular disease, Alzheimer's disease, dermatological disease and cancer.

The claimed compounds are preferably formulated prior to administration. Therefore, yet another embodiment of the present invention is a pharmaceutical formulation comprising a compound of Formula Ia and one or more pharmaceutically acceptable carriers, diluents or excipients.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient. The compositions are preferably formulated in a unit dosage form, each dosage containing from about 1 to about 20 mg, more usually about 2 to about 10 mg, of the active ingredient. However, it will be understood that the therapeutic dosage administered will be determined by the physician in the light of the relevant circumstances including the condition to be treated, the choice of compound to be administered and the chosen route of administration, and therefore the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

Formulation 1

Hard gelatin capsules are prepared using the following ingredients:

|  | Quantity (mg/capsule) |
| --- | --- |
| Active agent | 5 |
| starch, dried | 85 |
| magnesium stearate | 10 |
| Total | 100 mg |

The above ingredients are mixed and filled into hard gelatin capsules in 100 mg quantities.

Formulation 2

A tablet is prepared using the ingredients below:

|  | Quantity (mg/capsule) |
| --- | --- |
| Active agent | 7 |
| cellulose, microcrystalline | 78 |
| silicon dioxide, fumed | 10 |
| stearic acid | 5 |
| Total | 100 mg |

The components are blended and compressed to form tablets each weighing 100 mg.

Formulation 3

Tablets each containing 10 mg of active ingredient are made as follows:

|  | Quantity (mg/capsule) |
| --- | --- |
| Active agent | 10 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 100 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 100 mg.

Formulation 4

Capsules each containing 8 mg of medicament are made as follows:

|  | Quantity (mg/capsule) |
| --- | --- |
| Active agent | 8 mg |
| starch | 95 mg |
| microcrystalline cellulose | 95 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:
1. A salt of the Formula:

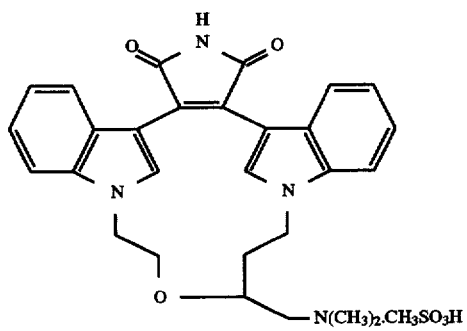

and solvates thereof.

2. A salt of claim 1 of the Formula:

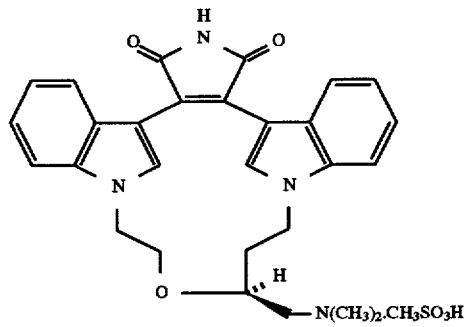

and solvates thereof.

3. A salt of claim 1 which is crystalline.
4. A salt of claim 2 which is crystalline.
5. A salt of claim 3, which is (S)-13-[(dimethylamino)methyl]-10,11,14,15-tetrahydro-4,9:16,21-dimetheno-1H,13H-dibenzo[E,K]pyrrolo[3,4-H][1,4,13]-oxadiazacyclohexadecine-1,3(2H)-dione methanesulfonate monohydrate.
6. A salt of claim 4, said salt having less than about 5% total related substances.
7. A salt of claim 5, said salt having less than about 5% total related substances.
8. A method of treating microvascular diabetic complications, which comprises administering to a mammal in need thereof, a pharmaceutically effective amount of a compound of claim 7.
9. A method of claim 8, wherein the pharmaceutically effective amount is 0.05 mg/kg/day to 0.25 mg/kg/day.
10. A pharmaceutical formulation comprising a salt of claim 1 together with one or more pharmaceutically acceptable diluents, excipients, or carriers.
11. A pharmaceutical formulation of claim 10, wherein the formulation comprises about 1 to about 20 mg of the salt.
12. A pharmaceutical formulation of claim 11, wherein the salt is

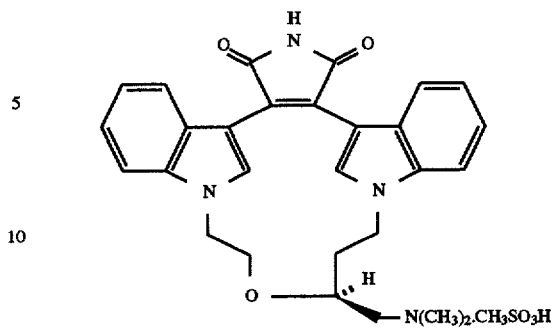

or solvates thereof.

13. A process for preparing a salt as claimed in claim 1, which comprises reacting a compound of the formula

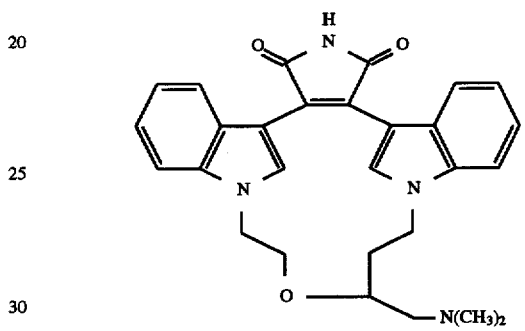

with methanesulfonic acid in a non-reactive organic solvent.

14. The process of claim 13, wherein the salt prepared is crystalline.
15. The process of claim 14, wherein the solvent is acetone-water.
16. The process of claim 15, wherein the solvent is about 5:1 to about 10:1 acetone to water by volume.
17. The process of claim 16, wherein the solvent is about 9:1 acetone to water by volume.
18. The process of claim 17, wherein the salt prepared is

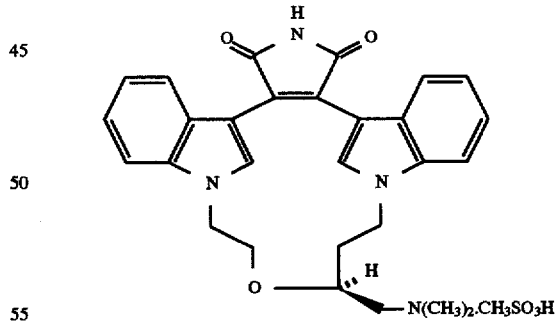

or solvates thereof.

* * * * *